(12) United States Patent
Nightingale et al.

(10) Patent No.: US 12,403,278 B2
(45) Date of Patent: Sep. 2, 2025

(54) APPARATUS AND METHOD FOR PROVIDING GASES TO A USER

(71) Applicant: Fisher & Paykel Healthcare Limited, Auckland (NZ)

(72) Inventors: Christopher Earl Nightingale, Auckland (NZ); Donald Roy Kuriger, Auckland (NZ)

(73) Assignee: Fisher & Paykel Healthcare Limited, Auckland (NZ)

(*) Notice: Subject to any disclaimer, the term of this patent is extended or adjusted under 35 U.S.C. 154(b) by 306 days.

(21) Appl. No.: 18/315,437

(22) Filed: May 10, 2023

(65) Prior Publication Data
US 2023/0390512 A1 Dec. 7, 2023

Related U.S. Application Data

(63) Continuation of application No. 16/289,262, filed on Feb. 28, 2019, now Pat. No. 11,684,734, which is a
(Continued)

(51) Int. Cl.
*A61M 16/00* (2006.01)
*A61B 5/00* (2006.01)
(Continued)

(52) U.S. Cl.
CPC ....... *A61M 16/0066* (2013.01); *A61B 5/4809* (2013.01); *A61M 16/0069* (2014.02);
(Continued)

(58) Field of Classification Search
CPC ..... A61B 5/4806–4818; A61B 5/4809; A61M 16/0066; A61M 16/0069; A61M 16/06;
(Continued)

(56) References Cited

U.S. PATENT DOCUMENTS 10,258,754 B2 4/2019 Nightingale et al.
11,684,734 B2 6/2023 Nightingale et al.
(Continued)

FOREIGN PATENT DOCUMENTS

EP 0788805 8/1997
WO WO 2005/089641 A1 9/2005
(Continued)

OTHER PUBLICATIONS

International Search Report; PCT/IB2011/002325; dated Feb. 8, 2012; 3 pages.
(Continued)

*Primary Examiner* — Elliot S Ruddie
(74) *Attorney, Agent, or Firm* — Knobbe Martens Olson & Bear LLP (57) ABSTRACT

Apparatus and methods are disclosed for controlling pressure delivery to a user such as a patient. A flow generator generates an outlet flow at an outlet port for delivery to a patient. At least one sensor measures properties of the flow of gas at the outlet port or being delivered to the patient. A controller is operatively connected to the flow generator and the at least one sensor, and is adapted to operate according to a pressure control mode in which the controller controls the flow generator to output a substantially steady pressure or a flow control mode in which the controller controls the flow generator to output a substantially steady flow. The controller operates in the flow control mode when a patient may be awake and in the pressure control mode when the patient may be asleep.

20 Claims, 5 Drawing Sheets

Related U.S. Application Data continuation of application No. 13/814,922, filed as application No. PCT/IB2011/002325 on Aug. 12, 2011, now Pat. No. 10,258,754.

(60) Provisional application No. 61/373,361, filed on Aug. 13, 2010.

(51) Int. Cl.
*A61M 16/06* (2006.01)
*A61M 16/10* (2006.01)
*A61M 16/16* (2006.01)

(52) U.S. Cl.
CPC .......... *A61M 16/06* (2013.01); *A61M 16/109* (2014.02); *A61M 16/16* (2013.01); *A61M 2016/0027* (2013.01); *A61M 2016/0039* (2013.01); *A61M 2205/3653* (2013.01); *A61M 2205/502* (2013.01)

(58) Field of Classification Search
CPC ................ A61M 16/109; A61M 16/16; A61M 2016/0027; A61M 2016/0039; A61M 2205/3653; A61M 2205/502; A61M 16/1085; A61M 16/1095; A61M 2016/0015; A61M 2016/003; A61M 2230/42; A61M 16/024; A61M 2205/3334; A61M 16/00
See application file for complete search history.

(56) References Cited

U.S. PATENT DOCUMENTS

| | | |
|---|---|---|
| 2005/0042589 A1 | 2/2005 | Hatlestad et al. |
| 2006/0102179 A1 | 5/2006 | Rapoport et al. |
| 2006/0272642 A1* | 12/2006 | Chalvignac ......... A61M 16/024 128/204.23 |
| 2007/0175473 A1 | 8/2007 | Lewis et al. |
| 2008/0202528 A1* | 8/2008 | Carter ................ A61M 16/026 128/204.23 |
| 2009/0149895 A1 | 6/2009 | Dacey, Jr. et al. |
| 2009/0205662 A1 | 8/2009 | Kwok et al. |
| 2010/0094366 A1 | 4/2010 | McCarthy |
| 2010/0252042 A1 | 10/2010 | Kapust et al. |

FOREIGN PATENT DOCUMENTS

| | | |
|---|---|---|
| WO | WO 2006/102708 A1 | 10/2006 |
| WO | WO 2008/028248 A1 | 3/2008 |
| WO | WO 2008/092021 A2 | 7/2008 |
| WO | WO 2009/145646 A1 | 12/2009 |
| WO | WO 2009/146484 A1 | 12/2009 |

OTHER PUBLICATIONS

Written Opinion; PCT/IB2011/002325; dated Feb. 8, 2012; 6 pages.
International Preliminary Report on Patentability in corresponding International Patent Application No. PCT/IB2011/002325, dated Feb. 28, 2013, in 8 pages.

* cited by examiner

APPARATUS AND METHOD FOR PROVIDING GASES TO A USER

CROSS-REFERENCE TO RELATED APPLICATIONS

This application is a continuation of U.S. patent application Ser. No. 16/289,262, filed Feb. 28, 2019, issued as U.S. Pat. No. 11,684,734, which is a continuation of U.S. patent application Ser. No. 13/814,922, filed Feb. 7, 2013, issued as U.S. Pat. No. 10,258,754, which is a national phase of International Application No. PCT/IB2011/002325, filed Aug. 12, 2011, which claims priority from U.S. Provisional Application No. 61/373,361, filed Aug. 13, 2010.

BACKGROUND

Field

The present disclosure generally relates to apparatus and methods for providing gases to a user. More particularly, certain aspects of the present disclosure relate to such apparatus used for providing pressure support to a sleeping user, such as in the treatment of obstructive sleep apnea.

Description of Related Art

A common method of treating obstructive sleep apnea (OSA) involves a pressure device that provides breathing gases, typically air, to a user (often referred to as the patient) while the user is asleep. The pressure device can be any of a number of units that fall into the broad classification of PAP (positive airway pressure devices) or CPAP (continuous PAP).

Within this broad classification, there are wide variations. For example, some units include a function to provide a different pressure during patient inspiration than during patient expiration (e.g., BiPAP), some units provide an auto-setting or autotitrating mode, where the supplied pressure varies through the period of use in response to detected events. In this context, detected events may include snoring, hypopneas, or obstructive breathing. Units also may respond to patient awakening and mask removal, for example, by reducing the delivered pressure. Other units deliver a predetermined set pressure, which may be delivered at the same pressure night after night, or may be varied night by night as adjusted by a physician, or as automatically adjusted by the unit. Many units include a ramp function that begins automatically or by patient selection. The ramp function causes the unit to commence at a low pressure, which is sometimes settable, and causes the unit gradually increase pressure toward a highest pressure, which may be the predetermined treatment pressure or an intermediate pressure.

The units typically provide controlled pressure delivery. For example, the units typically include a flow generator, a pressure sensor sensing the pressure being delivered to the user, and a feedback control controlling the output of the flow generator based on a sensor signal so that the sensed pressure is maintained close to a demand pressure. Alternatively, the flow generator can include a fan having a known pressure and flow response. The output of the flow generator can be controlled to deliver a desired pressure using feedback from a flow sensor in the circuit. Alternatively, the flow generator may include a fan that provides a substantially uniform pressure at a given rotation speed across a useful range of flow. Pressure then can be controlled by setting a substantially constant motor speed.

Even for a lower pressure, such as a pressure at the start of a ramp cycle, most of these units supply a minimum pressure of 3 cmH2O or more. This is more comfortable for the user than the full treatment pressure and is sufficient to provide a substantial flow of breathing gases through the supply line to the user, which breathing gases exit through a bias flow port or a controlled leak port provided at or near the user interface (e.g., mask).

SUMMARY

An object of the present disclosure is to provide apparatus or method for providing breathing gases to a user, which at least go some way toward improving on prior systems, or which will at least provide users with a useful choice.

According to one aspect, the present disclosure may broadly be said to consist in an apparatus comprising a flow generator generating an outlet flow at an outlet port for delivery to a patient, at least one sensor for measuring properties of the flow of gas exiting the flow generator through the outlet port at being delivered to the patient, a controller operatively connected to the flow generator and connected to the at least one sensor, the controller adapted to operate according to a pressure control mode in which the controller causes the flow generator to output a substantially steady pressure, or a flow control mode in which the controller controls the flow generator to output a substantially steady flow, and wherein according to a therapy mode of the controller, the controller operates in the flow control mode when a patient may be awake and in the pressure control mode when the patient may be asleep.

According to another aspect, the present disclosure may broadly be said to consist in an apparatus comprising a flow generator generating an outlet flow at an outlet port for delivery to a patient, at least one sensor for measuring properties of the flow of gas exiting the flow generator through the outlet port or being delivered to the patient, a controller operatively connected to the flow generator and connected to the at least one sensor, the controller adapted to operate according to a pressure control mode in which the controller causes the flow generator to output a substantially steady pressure, or a flow control mode in which the controller controls the flow generator to output a substantially steady flow, wherein according to at least one therapy mode the controller operates initially in the flow control mode and subsequently switches into the pressure control mode once the controller determines the patient may be asleep.

According to another aspect, the present disclosure may broadly be said to consist in an apparatus comprising a flow generator generating an outlet flow at an outlet port for delivery to a patient, at least one sensor for measuring properties of the flow of gas exiting the flow generator through the outlet port or being delivered to the patient, a controller operatively connected to the flow generator and connected to the at least one sensor, the controller adapted to operate according to a pressure control mode in which the controller causes the flow generator to output a substantially steady pressure, or a flow control mode in which the controller controls the flow generator to output a substantially steady flow, and wherein the controller switches from the pressure control mode to the flow control mode when analysis of input from the at least one sensor indicates patient arousal.

According to a further aspect the controller operates initially in the flow control mode and subsequently switches into the pressure control mode once the controller determines the patient may be asleep.

According to a further aspect the controller determines that the patient may be asleep by analyzing input from the at least one sensor.

According to a further aspect the controller analyzes parameters of the delivered flow to determine the presence of sleep disordered breathing events, and determines that a patient may be asleep by the presence of sleep disordered breathing events.

According to a further aspect the controller determines that the patient is asleep if predetermined number of events have occurred over a predetermined preceding amount of time.

According to a further aspect the controller switches from the pressure control mode to the flow control mode when analysis of input from the at least one sensor indicates patient arousal.

According to a further aspect, in the pressure control mode, the controller maintains a demand pressure value, analyzes input from the sensor to determine a current pressure value, and administers feedback control to the flow generator according to the demand pressure value and the current pressure value.

According to a further aspect the feedback control of the flow generator is based on the difference between the demand pressure value and the current pressure value.

According to a further aspect, in the flow control mode, the controller analyzes input from the at least one sensor and determines a flow rate value and controls the flow generator based on the determined flow rate value and a desired flow rate.

According to a further aspect the controller controls the flow generator based on the flow rate value and a desired flow rate range, increasing an input parameter of the flow generator (intended to result in an increased output of the flow generator) when the flow rate value is lower than the range, and decreasing an input parameter of the flow generator (intended to result in a decrease in the output of the flow generator) when the flow rate value is above the flow rate range.

According to a further aspect the controller switches to the pressure control mode if both the flow rate value is below the flow range and an input parameter to the flow generator above a predetermined value.

According to a further aspect the input parameter to the flow generator, when in the flow control mode, is a command motor speed.

According to a further aspect, upon entering the flow control mode, the controller sets an initial command motor speed for the flow generator and progressively increases the command motor speed from the initial command motor speed when (or while) the flow rate value is (or remains) below a lower threshold value, or decreases the command motor speed from the initial command motor speed when (or while) the flow rate value is (or remains) above an upper threshold value.

According to a further aspect the controller returns the command motor speed to the initial command motor speed when the flow rate value exceeds the upper threshold value.

According to a further aspect the lower threshold value is above 15 liters per minute.

According to a further aspect the upper threshold value is above 17 liters per minute.

According to a further aspect the controller operates in the flow control mode when the controller determines that the patient is awake.

According to a further aspect the controller operates in the pressure control mode when the controller determines that the patient is asleep.

According to a further aspect the controller stores data representing that the patient is awake or asleep, and the controller operates in the flow control mode when the data indicates that the patient is awake, and the controller operates in the pressure control mode when the data indicates that the patient is asleep.

According to a further aspect the controller operates in the flow control mode for an initial period of time (which may be expected to be sufficient for the patient to fall asleep).

According to a further aspect the controller subsequently switches to the pressure control mode.

According to a further aspect the controller stores data indicating a probability that the patient is awake, data indicating a probability that the patient is asleep, or both, and the controller operates in the flow control mode or in the pressure control mode based on the stored probability data.

According to a further aspect the controller is adapted to operate the flow generator in a test mode, in which an elevated pressure flow is provided for a period of time, followed by operating in the flow control mode.

According to a further aspect the controller operates in the test mode according to selection by a user, or automatically at the commencement of therapy, or both.

According to a further aspect the controller operates in the test mode to provide a pressure at a preset level or at a level based on prior historical data of use of the apparatus.

According to a further aspect the controller varies an input parameter to the flow generator according to the respiratory phase of the user during the flow control mode such that the delivered flow during patient inhalation is boosted relative to the flow that would be delivered during inhalation of the control parameter to the flow generator were maintained constant.

According to a further aspect the controller determines indications of insufficient delivered flow during inhalation and delivers boosted inhalation flow in response to the determination.

According to a further aspect the controller monitors a measured pressure and delivers boosted inhalation flow when a pressure at the mask is at or below 0 cmH2O.

According to a further aspect the controller monitors delivered flow, pressure, or both in the flow control mode and adapts the delivered flow when there are indications of potential starvation.

According to another aspect, the present disclosure may broadly be said to consist in a method comprising generating an outlet flow at an outlet port for delivery to a patient, measuring properties of the flow of gas exiting the flow generator through the outlet port or being delivered to the patient, selectively controlling the output of the flow generator according to a pressure control mode to output a substantially steady pressure or according to a flow control mode to output a substantially steady flow, and operating in the flow control mode when a patient may be awake and in the pressure control mode when the patient may be asleep.

According to another aspect, the present disclosure may broadly be said to consist in a method comprising generating an outlet flow at an outlet port for delivery to a patient, measuring properties of the flow of gas exiting the flow generator through the outlet port or being delivered to the patient, selectively controlling the output of the flow generator according to a pressure control mode to output a substantially steady pressure or according to a flow control mode to output a substantially steady flow, and operating initially in the flow control mode and subsequently switching into the pressure control mode after determining the patient may be asleep.

According to another aspect, the present disclosure may broadly be said to consist in a method comprising generating an outlet flow at an outlet port for delivery to a patient, measuring properties of the flow of gas exiting the flow generator through the outlet port or being delivered to the patient, selectively controlling the output of the flow generator according to a pressure control mode to output a substantially steady pressure or according to a flow control mode to output a substantially steady flow, and switching from the pressure control mode to the flow control mode when analysis of input from the at least one sensor indicates patient arousal.

According to a further aspect, the method includes operating initially in the flow control mode and subsequently switching into the pressure control mode after determining the patient may be asleep.

According to a further aspect, the method includes determining that the patient may be asleep by analyzing one or more parameters of the flow being delivered to the patient.

According to a further aspect, the method includes analyzing parameters of the delivered flow to determine the presence of sleep disordered breathing events, and determining that a patient may be asleep by the presence of sleep disordered breathing events.

According to a further aspect, the method includes determining that the patient is asleep if a predetermined number of events have occurred over a predetermined preceding amount of time.

According to a further aspect, the method includes switching from the pressure control mode to the flow control mode when analysis of input from the at least one sensor indicates patient arousal.

According to a further aspect, the method includes, in the pressure control mode, maintaining a demand pressure value, analyzing input from the sensor to determine a current pressure value and administering feedback control to the flow generator according to the demand pressure value and the current pressure value.

According to a further aspect, the feedback control of the flow generator is based on the difference between the command pressure value and the current pressure value.

According to a further aspect, the method includes, in the flow control mode, analyzing input from the at least one sensor and determining a flow rate value and controlling the flow generator based on the determined flow rate value and a desired flow rate.

According to a further aspect, the method includes controlling the flow generator based on the flow rate value and a desired flow rate range, increasing an input parameter of the flow generator (intended to result in an increased output of the flow generator) when the flow rate value is lower than the flow rate range and decreasing an input parameter of the flow generator (intended to result in a decrease in the output of the flow generator) when the flow rate value is above the flow rate range.

According to a further aspect, the method includes switching to the pressure control mode if the flow rate value is below the flow rate range and an input parameter to the flow generator is above a predetermined value.

According to a further aspect, the input parameter to the flow generator, when in the flow control mode, is a command motor speed.

According to a further aspect, the method includes, upon entering the flow control mode, setting an initial command motor speed for the flow generator and progressively increasing the command motor speed from the initial command motor speed when or while the flow rate value is or remains below a lower threshold value.

According to a further aspect, the method includes returning the command motor speed to the initial command motor speed when the flow rate value exceeds the upper threshold value.

According to a further aspect, the lower threshold value is above 15 liters per minute.

According to a further aspect, the upper threshold value is above 17 liters per minute.

According to a further aspect, the method includes operating in the flow control mode after determining that the patient is awake.

According to a further aspect the method includes operating in the pressure control mode after determining that the patient is asleep.

According to a further aspect, the method includes storing data representing that the patient is awake or asleep, and operating in the flow control mode when the data indicates that the patient is awake, and operating in the pressure control mode when the data indicates that the patient is asleep.

According to a further aspect, the method includes operating in the flow control mode for an initial period of time (which may be expected to be sufficient for the patient to fall asleep).

According to a further aspect, the method includes subsequently switching to the pressure control mode.

According to a further aspect, the method includes storing data indicating a probability that the patient is awake, data indicating a probability that the patient is asleep, or both, and operating in the flow control mode or in the pressure control mode based on the stored probability data.

According to a further aspect, the method includes operating the flow generator in a test mode, in which an elevated pressure or flow is provided for a period of time, followed by operating in the flow control mode.

According to a further aspect, the method includes operating in the test mode according to selection by a user, or automatically at the commencement of therapy, or both.

According to a further aspect, the method includes operating in the test mode to provide a pressure at a preset level, or at a level based on prior historical data.

According to a further aspect, the method includes varying an input parameter to the flow generator according to the respiratory phase of the user during the flow control mode such that the delivered flow during patient inhalation is boosted relative to the flow that would be delivered during inhalation if the control parameter to the flow generator were maintained constant.

According to a further aspect, the method includes determining indications of insufficient delivered flow during inhalation and delivers boosted inhalation flow in response to the determination.

According to a further aspect, the method includes monitoring a measured pressure and delivering boosted inhalation flow when a pressure at the mask is at or below 0 cmH2O.

According to a further aspect, the method includes monitoring delivered flow, pressure, or both in the flow control mode and adapting the delivered flow when there are indications of potential starvation.

To those skilled in the art to which the disclosure relates, many changes in construction and widely differing embodiments and applications of the disclosure will suggest themselves without departing from the scope of the disclosure as defined in the appended claims. The disclosures and the descriptions herein are purely illustrative and are not intended to be in any sense limiting.

The term "comprising," as used in the specification and claims, means "consisting at least in part of." When interpreting a statement in this specification and claims that includes "comprising," features other than that or those prefaced by the term may also be present. Related terms such as "comprise" and "comprises" are to be interpreted in the same manner.

DETAILED DESCRIPTION

Certain features, aspects and advantages of an embodiment of the present disclosure provide an alternative to a defined pressure ramp. The mode according to certain features, aspects and advantages of an embodiment of the present disclosure provides a sub-therapeutic pressure at the beginning of the session or at times when the apparatus considers the user to be awake. This mode may be selectable by a user, may be selectable by an overall control algorithm of the apparatus, or may be an automatic function at the beginning of every session of use of the apparatus. Once the user is asleep, or after an initial period of sub-therapeutic delivery, the apparatus delivers a therapeutic pressure.

As used herein, sub-therapeutic pressures mean pressures below about 4 cmH2O, preferably pressures below about 3 cmH2O and most preferably pressures below about 2 cmH2O.

According to certain features, aspects and advantages of an embodiment of the present disclosure, sub-therapeutic pressure can be provided to the user in conjunction with monitoring the flow delivered to the user. The flow delivered to the user is monitored (e.g., a controller of the apparatus monitors the flow delivered to the user) and the flow generator is adjusted to avoid flow rates that may be insufficient to provide proper scavenging of the patient interface. In some embodiments, the controller of the apparatus monitors the flow and adjusts the flow generator. The control preferably can avoid the average flow rate falling below about 10 liters per minute, preferably avoids the average flow rate falling below about 12 liters per minute, and most preferably avoids the average flow rate falling below about 15 liters per minute.

For a given user interface, a particular flow rate may be considered sufficient to provide appropriate scavenging. Across most patient interfaces presently available, an average flow rate of about 15 liters per minute is thought to be sufficient. Whatever the chosen sufficient flow rate, the apparatus, while in the sub-therapeutic mode, preferably adjusts operation of the flow generator to maintain the average flow rate close to the chosen sufficient flow rate. For example, the controller may maintain the average flow within about 5 liters per minute of the chosen sufficient flow rate, or most preferably, within about 2 liters per minute of the chosen sufficient flow rate.

By way of example, the controller of the apparatus can control the flow generator by controlling the power input to the flow generator. Thus, in the sub-therapeutic mode, the controller may decrease power input to the flow generator when the measured average flow exceeds the desired flow range and may increase power input to the flow generator when the average flow is below the desired flow range.

Alternatively, the controller of the apparatus can control some other parameter of the flow generator (e.g., motor speed). Thus, the controller may command an increase in motor speed if the flow is below the desired range and may command a decrease in motor speed if the flow is above the desired range.

Alternatively, the flow generator may include a pressure source and a pressure regulator. Thus, the controller may reduce the set pressure of the pressure regulator when the measured flow is above the desired range and may increase the set pressure of the pressure regulator when the flow is below the desired range.

According to certain features, aspects and advantages of an embodiment of the present disclosure, the apparatus can operate in the sub-therapeutic delivery mode during periods where the user is awake while operating in a therapeutic delivery mode when the user is asleep.

Accordingly, the controller may provide an initial period of operation in the sub-therapeutic mode during each session of use. In addition, in an apparatus that includes functions for determining that the user is awake, this feature may also be used during periods within the session when the user has been determined to be awake. For example, the Fisher & Paykel Healthcare SleepStyle™ HC250 AutoCPAP device with the Sensawake™ function determines instances of user arousal and reduces the delivered pressure to a pre-set awake pressure once the patient is determined likely to be awake. Implementing certain features, aspects and advantages of the present disclosure in such a device, the device would, after reaching the awake pressure, enter the sub-therapeutic mode.

In the sub-therapeutic mode, the control aims cause the flow generator to maintain a substantially steady flow at a flow level that is selected to be sufficient to result in appropriate flushing of the user interface. As used herein, a substantially steady flow means that the average flow over a period of multiple breaths (e.g., about 20 seconds) remains substantially constant or within a limited range (e.g., within a range of up to about 5 liters per minute) despite changing system conditions. Changing system conditions can include, for example, changing leak conditions due to changes in the efficiency of sealing of the user interface. By way of clarification and comparison, changes in system conditions that would see an increase in flow under a constant pressure controlled system of greater than about 5 liters per minute, are responded to with a substantially steady flow in the sub therapeutic mode.

In the therapeutic mode, the controller causes the flow generator to deliver a substantially steady pressure. The controller may use a pressure feedback control, or the substantially steady pressure may be the result of a blower with a steady pressure output for a given operating speed, for example but without limitation. Like substantially steady flow, substantially steady pressure refers to the average pressure over multiple breaths.

Figure 1:
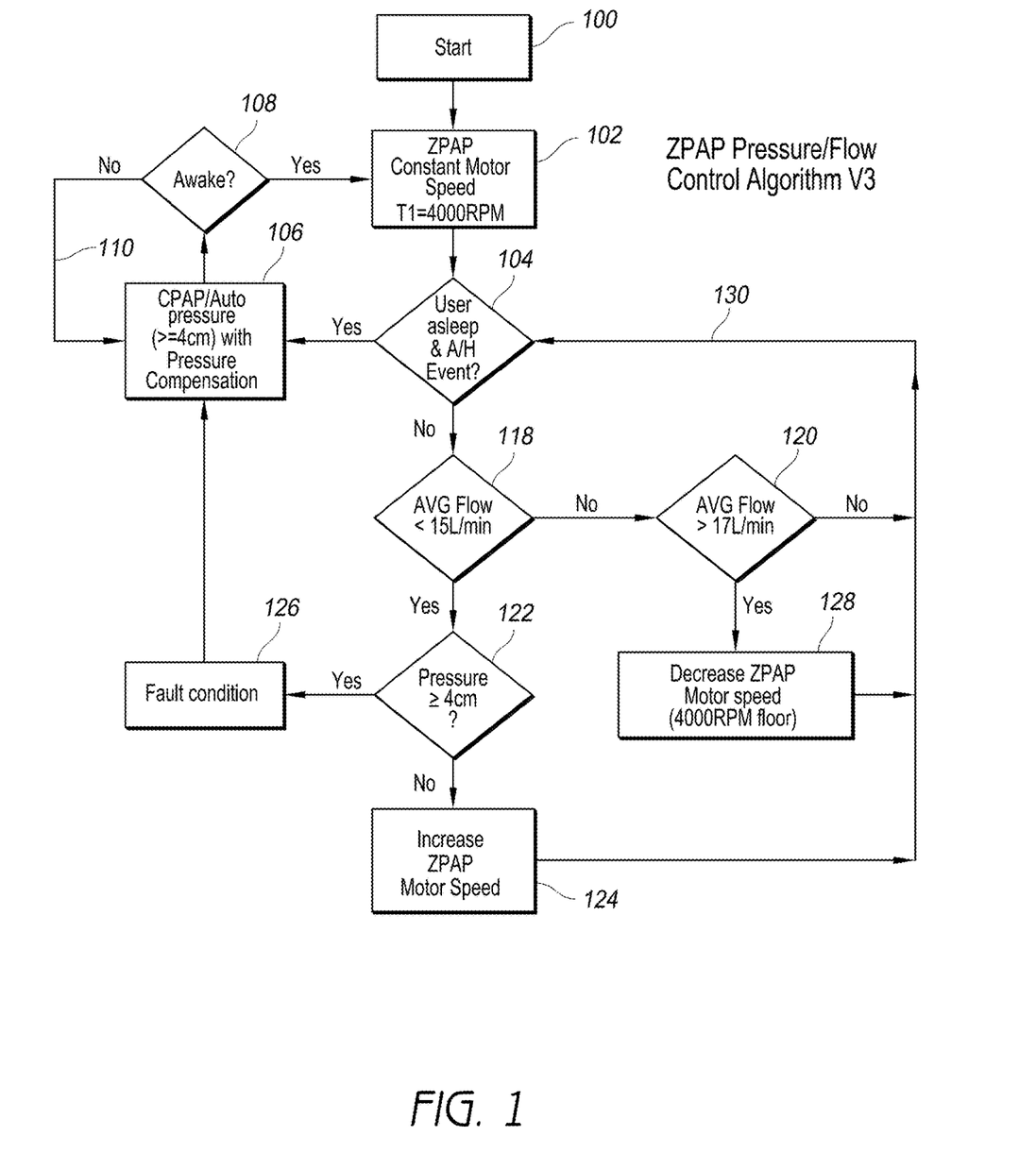
FIG. 1 is a flow diagram illustrating a control method according to certain features, aspects and advantages of the present disclosure, which control method can be implemented by a controller of an appropriate gas supply apparatus.

One example control method that is arranged and configured in accordance with certain features, aspects and advantages of an embodiment of the present disclosure is illustrated in FIG. 1. The illustrated control method can be incorporated in any suitable apparatus, including but not limited to the apparatus schematically shown in FIG. 2.

The illustrated method for implementing the sub-therapeutic mode commences at step 100. Step 100 may be triggered by a conscious user choice, for example, selecting a control mode using the electronic user control interface. Alternatively, the mode may be an initial starting mode for the apparatus or may be commenced by the apparatus according to elements of a wider control strategy.

The method proceeds to step 102 and a control command is issued to the flow generator to cause the flow generator to operate at an initial level. In the illustrated embodiment, the controller supplies a command motor speed as an input to the flow generator and a motor of the flow generator is speed-controlled to the command motor speed. Other configurations can provide command pressures, command flow values or motor power input as input parameters, for example but without limitation.

Preferably, the initial command input parameter for the flow generator is at a level that would usually provide a sub-therapeutic pressure between about 0.2 cmH2O and about 2 cmH2O with the user interface (e.g., mask) correctly fitted to the user.

The method proceeds to step 104. At step 104, a determination is made whether the user is asleep. Preferably, the controller maintains a value representing the controller's belief that the user is asleep or awake. The value may be a probability assessed by the controller of whether the patient is asleep or awake, for example but without limitation. The probability can be assessed against criteria at step 104 to decide whether to proceed on the basis that the patient is asleep or to decide whether to proceed on the basis that the patient is awake. The value may be maintained by, for example but without limitation, assessing recent breathing patterns of the user, assessing recent history of apneaic events and/or assessing recent history of obstructed breathing of the user. Data may be examined, for example, over a time period covering the preceding few minutes, ten minutes or other suitable time period.

Alternatively, the controller may maintain a timer that is started when the machine is turned on, or that is started or reset with each conscious user interaction with the device (e.g., activating a button on the user interface), and the decision whether the user is asleep is made by comparing the elapsed time indicated by the timer with a threshold period of time. Effectively, in such a configuration, the controller assumes that the person may be awake for an initial period after the most recent interaction, and assumes that the user may be asleep after that period has elapsed. The period may be fixed, settable or adaptive. For example, the period may be a predetermined period preset in the device according to typical or average user sleep patterns. Alternatively, the period may be a user or physician setting, settable through the electronic user control interface or with transmitted prescription data. Alternatively, the controller may maintain a data value from session to session and adapt the period according to user response in previous sessions. For example, the controller may adapt the period in response to measures of user compliance. In other words, if user compliance is low (e.g., the user does not use the device for extended periods), the period may be increased to provide low pressures to enhance comfort and encourage improved user compliance.

Alternative methods of making a determination that the patient is asleep or is awake are described in other patent publications, for example U.S. Pat. No. 6,988,994 and US 2008/0092894, each of which are hereby incorporated by reference in their entirety.

These assessments, and the maintenance of a sleeping value, may be made according to a separate control program running in parallel with the control program described with reference to FIG. 1. The separate control programs may be generally separate subroutines that may be executed sequentially in a given execution cycle, but that broadly operate in parallel. In that case, the control program of FIG. 1, at step 104, may determine whether the user is asleep or awake based on a input parameter maintained by this other control program, for example but without limitation.

If the program determines at step 104 that the user is asleep, then at step 106, the method proceeds to apply a therapeutic pressure (i.e., enters a therapeutic mode). This may be commenced at step 106, for example, by immediately proceeding to a predetermined starting point pressure (e.g., about 3 cmH2O or greater). This pressure may be a preset of the device or may be a variable pressure set by a physician. Alternatively, the method may proceed directly to a full treatment pressure, for example but without limitation, a treatment pressure prescribed by a physician and/or preconfigured in the device. Alternatively, the method may proceed to an automatic titrating mode, which commences at a starting therapeutic pressure and adjusts the supply pressure according to breathing events such as apneas, hypopneas, flow obstructions, and periods of normal breathing.

In the therapeutic mode, the method preferably seeks to maintain a substantially steady pressure.

For example, the controller may control the flow generator based on input from a pressure sensor that senses pressure in the user interface (e.g., by being positioned directly in the user interface, by interfacing with a part of the flow path to the user interface that is downstream of the flow generator, or the like) such that the controller can use feedback from the pressure sensor to control the speed or power input to the flow generator or to control the input parameter of a pressure regulator, for example but without limitation.

Alternatively, the substantially steady flow can be derived from use of a fan having a substantially constant pressure output for a given fan speed across a wide range of flow, or from a self-regulating pressure regulator which, for example but without limitation, use a mechanically operative feedback control to adjust the pressure output according to a particular input parameter.

The therapeutic mode (e.g., CPAP or auto-titrating) may proceed according to any suitable treatment program and methods. Control of the particular applied pressure in these program and methods may be by a separate control program or routine running in parallel with the control program described with reference to FIG. 1.

The control method proceeds from step 106 to step 108 in a control loop that is intended to detect and respond to the awakening of a patient. For example, this would depend on the output of the separate control loop that determines on a continuous basis an awake state of the patient.

If the patient is still asleep, the method continues, as indicated by path 110, to apply the therapeutic treatment pressure at step 106. Preferably, the control loop of steps 106, 108 and 110 continues until the control method determines at step 108 that the patient has awakened. If the method determines at step 108 that the patient is awake, the method returns to step 102 to re-initiate the sub-therapeutic mode by changing the input parameter to the flow generator such that the flow generator provides gases at a sub-therapeutic pressure and progressing to step 104.

If at step 104 the method determines that the user is awake, then instead of proceeding to step 106, the method proceeds to step 118.

At steps 118, 120 and 122, the method checks a measure of the flow provided against a preferred flow range and at steps 124 and 128 adjusts the input parameter to the flow generator accordingly.

Preferably, at step 118, the method checks an assessed flow against a lower pressure value. For example, the method checks whether the recent average flow (e.g., the average flow over the preceding 5 breaths, 10 breaths, 10 seconds, 30 seconds or a suitable period) is less than the lower threshold.

The lower threshold value may be a fixed predetermined value. For example, the lower threshold value may be chosen to be suitable for all known user interfaces. Alternatively, the lower threshold value may be a settable value, for example, so that it can be set to correspond to a particular interface used by the user. Alternatively, the lower threshold value may be taken from a table of values based on a determined identity of the user interface (e.g., mask), or might be assessed or determined for a particular user interface in a test mode performed by the supply apparatus.

In the simplest case, a fixed preset flow value is thought sufficient to provide a significant improvement in comfort over prior arrangements without compromising safety, for example, by using a lower limit flow value of about 15 liters per minute.

If at step 118 the assessed average flow rate is less than the lower threshold level, the control method adjusts the input parameter to the flow generator to increase the output of the flow generator. For example but without limitation, the controller may increase a demand motor speed at step 124.

An additional check may be provided after determining that the average flow is below the lower control limit (e.g., lower than about 15 liters per minute) to determine whether the pressure has reached a therapeutic pressure level. For example, a step 122 may be provided after step 118. In some configurations, the pressure level can be checked before the output from the flow generator is adjusted (e.g., step 122 may be between steps 118 and 124).

At step 122, the method checks an assessed pressure in the user supply against a pressure threshold, for example about 4 cmH2O. If the flow is assessed below the lower limit at step 118 and the pressure is assessed above the threshold at step 122, the method preferably proceeds to leave the sub-therapeutic mode and switch control to the therapeutic mode, as discussed with reference to step 106. Under such a condition, the control method also may set a fault condition, for example but without limitation, as shown at step 126. The controller may provide an indication of the fault condition as an alert on the user control interface of the device or may record the fault condition in a session data log maintained by the device for later review by the user, physician or other interested party.

The control method can increase the flow generator output at step 124, for example but without limitation, by increasing the demand parameter for the flow generator. The increase may be a fixed predetermined incremental increase, an incremental increase that varies according to the present value of the parameter, or an incremental increase that varies according to the difference between the present value of the average flow and the desired flow range. For example but without limitation, the new input parameter (e.g., the new motor speed in a control motor speed embodiment) may be a function of the present motor speed, the present average flow value and a desired average flow value.

Alternatively, if at step 118 the average flow value is above the minimum range value, the control method checks the average flow value against an upper flow value threshold for the range.

Preferably, to maintain a low sub-therapeutic pressure, the flow range between the minimum value and maximum value is kept to low or a minimum. For example, the flow range (i.e., the difference between the upper threshold and the lower threshold) may be about 5 liters per minute or less, preferably about 3 liters per minute or less, and most preferably about 2 lines per minute or less.

In some configurations, both upward and downward adjustment of the control parameter for the flow generator can be made based on a single desired average flow value. Such configurations are particularly suitable if an adjustment increment for the control parameter is a function of the difference between the present average flow value and the desired average flow value. In such methods, the step 120 can be removed with the method proceeding directly from step 118 to step 128 if the average flow value is not less than the desired flow value. This alternative will lead to frequent adjustment of the motor input parameter, but if the frequent adjustments are small, they may be subtle enough to not significantly disturb the user.

If the average flow is above the preferred range at step 120 (or at step 118 according to the modified method discussed above), then at step 128, the control method decreases the input parameter to the flow generator. For example but without limitation, the decrease may be a predetermined increment, or an increment that is varied according to the present average flow, the present value of the input parameter or the difference between the present average flow and the desired average flow range. The method then returns to step 104. The steps 104, 118, 124, 120 and 128 broadly constitute a feedback control that controls the output of the flow generator according to a desired flow rate (or a desired flow rate range) and based on an assessed average flow rate value.

Figure 2:
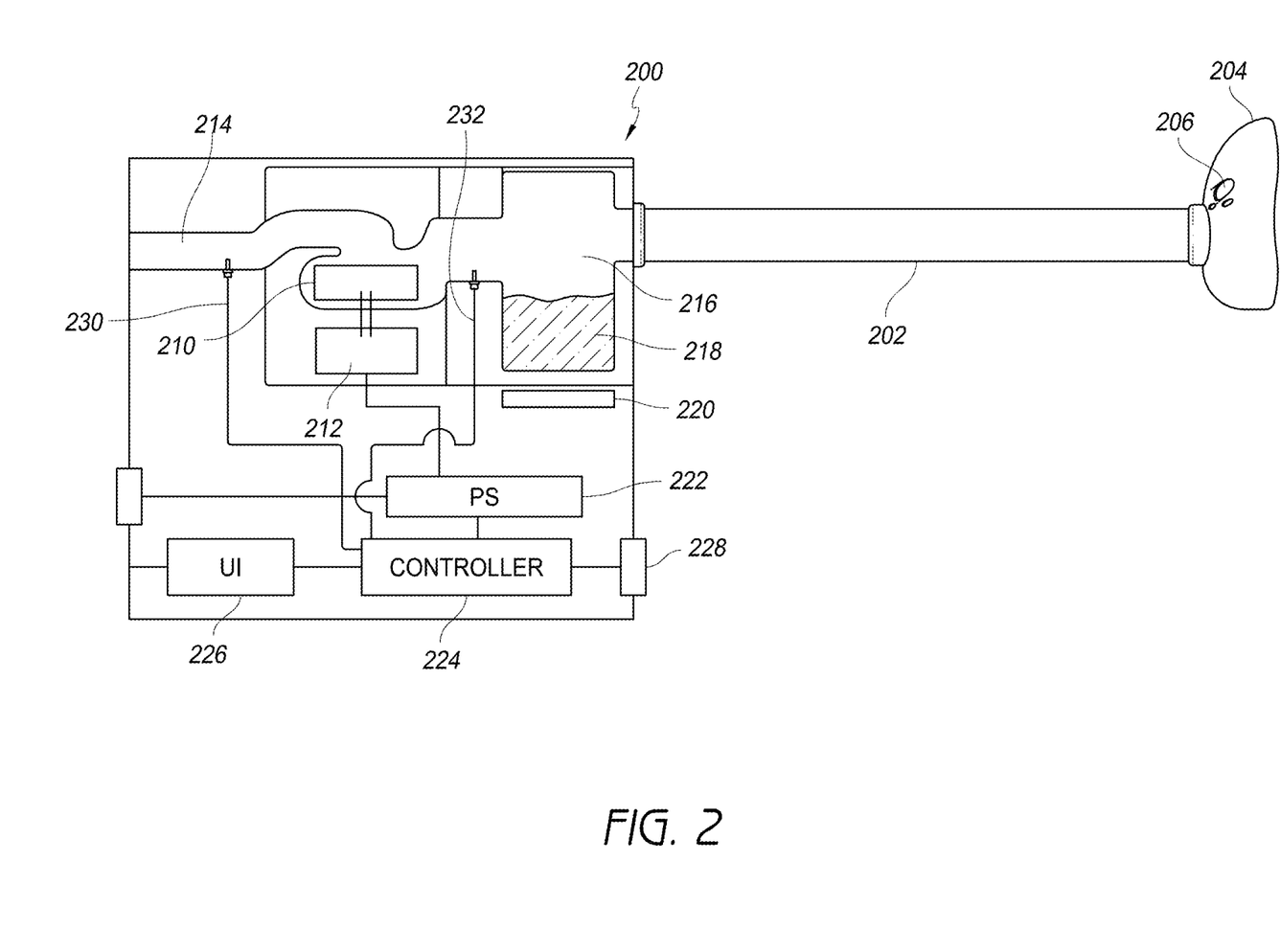
FIG. 2 is a block diagram illustrating a gases supply system that is arranged and configured in accordance with certain features, aspects and advantages of the present disclosure, which gases supply system can be used to implementing the control method, such as the control method shown in FIG. 1.

FIG. 2 is a schematic diagram illustrating a breathing gases supply system incorporating a control regimen that is arranged and configured in accordance with certain features, aspects and advantages of the present disclosure. The system preferably includes an apparatus 200 that delivers a supply of breathing gases, a supply conduit 202 and a user interface 204. The supply conduit 202 extends from an outlet of the gases supply apparatus 200 to the patient interface 204.

The patient interface 204 preferably includes a bias flow vent 206 that provides a controlled leak from the patient interface 204. The controlled leak allows the inside of the user interface 204 to be continuously flushed by fresh gases supplied by the supply apparatus 200. The user interface 204 may comprise any of the many types of typical user interfaces for PAP delivery, which can include, for example but without limitation, nasal masks, full face masks, oral masks, oral interfaces, nasal pillows, nasal seals or nasal cannula.

The bias flow vent 206 may be located directly on the user interface 204, may be positioned generally adjacent the user interface 204 on a connector between the user interface 204 and the supply tube 202 or may extend through the wall of the supply tube 202 at a location close to the user interface 204.

The supply apparatus 200 includes a flow generator. The preferred flow generator comprises a fan 210 driven by an electric motor 212. Air is drawn through an inlet 214 in the housing of the apparatus by the fan 210. Pressurized air leaves the fan 210 for supply to the user. In some configurations, controllable flow generators may draw on a source of high pressure gas and can regulate a flow of gas from the high pressure source.

The apparatus 200 may include a humidifier 216, for example but without limitation, in the form of a pass-over humidifier where air passing through a chamber of the humidifier 216 picks up a quantity of water vapor from a water reservoir 218. The water reservoir 218 may be heated by a heater 220. The humidifier may be integrated with the housing of the flow generator or may be a separate, and sometimes optional, component.

The heater 220 and the motor 212 are supplied with power from a power supply 222. The amount of power supplied to the motor 212 and the amount of power supplied to the heater 220 can be controlled by outputs of a controller 224. Preferably, the controller 224 also can be supplied with power from the power supply 222.

The controller 224 receives input from a user control interface 226. The controller 224 also is provided with an interface 228 for connecting with an external data source. The external data source may, for example but without limitation, be a communication interface, such as a modem or the like, or may be an interface to an external memory, such as a smart card, disk drive, flash memory or the like. For generic use, the interface 228 may be a data communication port according to any of the many available standards, such as, for example but without limitation, a universal serial bus (USB) port. A USB interface or the like can be used for connecting a wide range of peripheral devices.

The controller 224 preferably includes an embedded microcomputer with stored control program. In addition, the controller preferably includes interfaces for receiving input from the user control interface 226 and for receiving input from one or more sensors, which preferably include a flow sensor 230 and which also may include a pressure sensor 232 that can be located downstream of the fan 210. The flow sensor 230 can be upstream or downstream of the fan 210.

In some embodiments, the apparatus can be configured to perform control methods in the form of a control programs executable by the microcomputer of the controller 224.

In some embodiments, the controller 224 may comprise a fixed electronic circuit implementing the control programs, or a programmed logic circuit (e.g., an FPGA) implementing one or more control programs. Electronic circuits and logic circuits implementing the control program may be readily devised by persons skilled in the art.

This apparatus, operating according to the control method described above provides a sub-therapeutic mode of operation that is applied to the user while the user is awake. Breathing at this lower pressure may be less arduous than at the low therapeutic pressures applied at the commencement of therapy by prior art devices. This may be more comfortable and pleasant for the end user, improving therapy acceptance and compliance.

At the same time, a minimum flow is provided to supply an adequate flow of fresh breathing gases to flush the patient interface and reduce patient re-breathing. Advantageously the system preferably is not mask dependent. A large range of masks may be utilized with the apparatus according to the present disclosure.

Upon the detection of sleep, or a breathing disorder event, the apparatus will increase the delivered pressure to a predetermined or automatically determined therapeutic level at a comfortable and tolerable rate. At this stage, the user preferably is asleep. Accordingly, the user should not be aware of or consciously experience the required higher therapeutic pressures, again hopefully improving compliance.

If a user wakes during the session, the apparatus will revert to the sub-therapeutic state. The now conscious user will not experience, or will only experience for a limited time, the higher therapeutic pressures that are supplied while they are asleep because the unit returns to the sub-therapeutic state. This should also increase user compliance, particularly in the later stages of a sleep session, where the user otherwise may remove and cast aside the patient interface before trying to return to sleep.

Figure 3A:
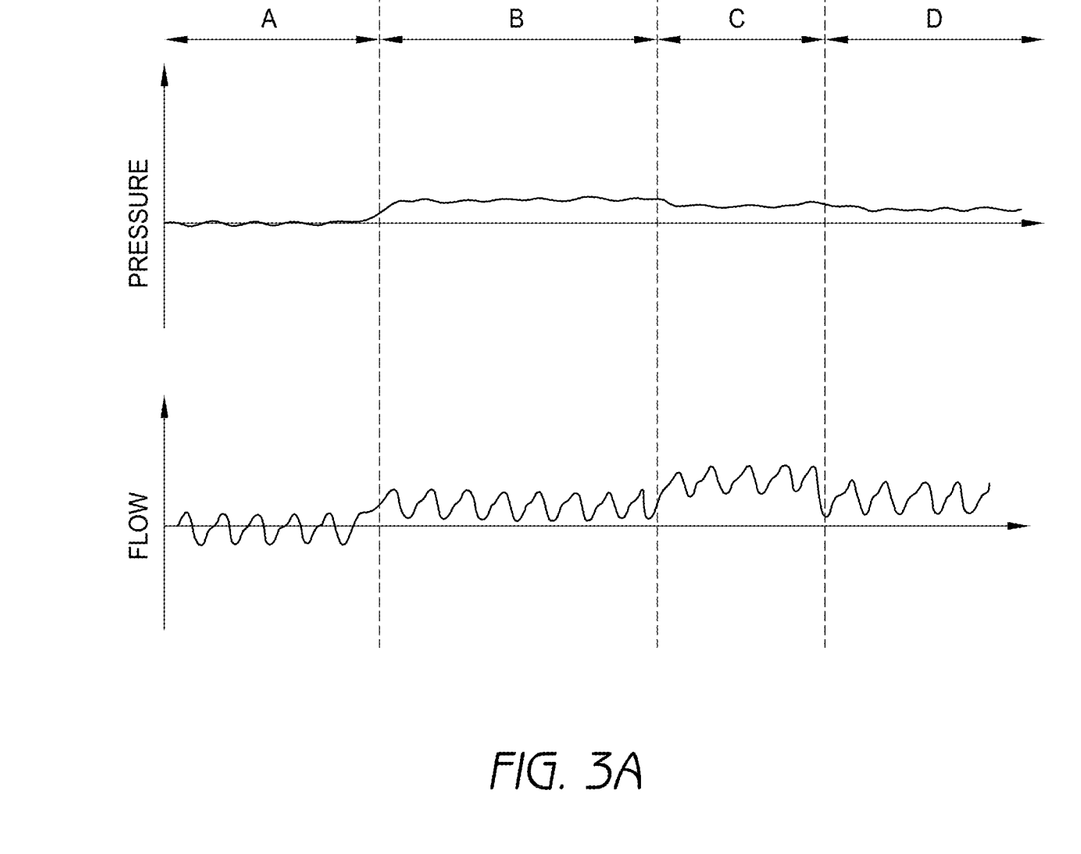
FIG. 3A is an example of a representative plot of pressure and flow against time for part of a session of use of an apparatus implementing a control method that is arranged and configured in accordance with certain features, aspects and advantages of the present disclosure. The plot of FIG. 3A shows a period in which flow is adjusted to reach a desired average flow, subsequent to which a leak develops.
Figure 3B:
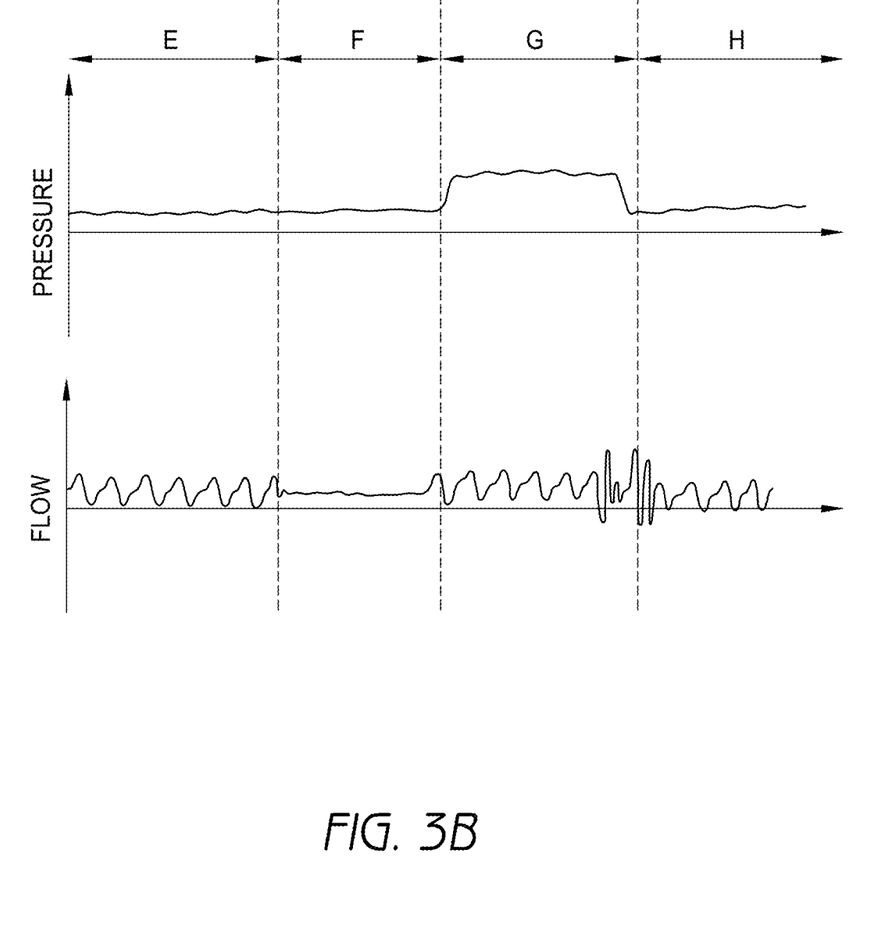
FIG. 3B is an example of a representative plot of pressure and flow against time for another part of a session of use of an apparatus implementing a control method that is arranged and configured in accordance with certain features, aspects and advantages of the present disclosure. The plot of FIG. 3B shows a period in which the user has an apnea followed by an arousal or awakening.
Figure 3C:
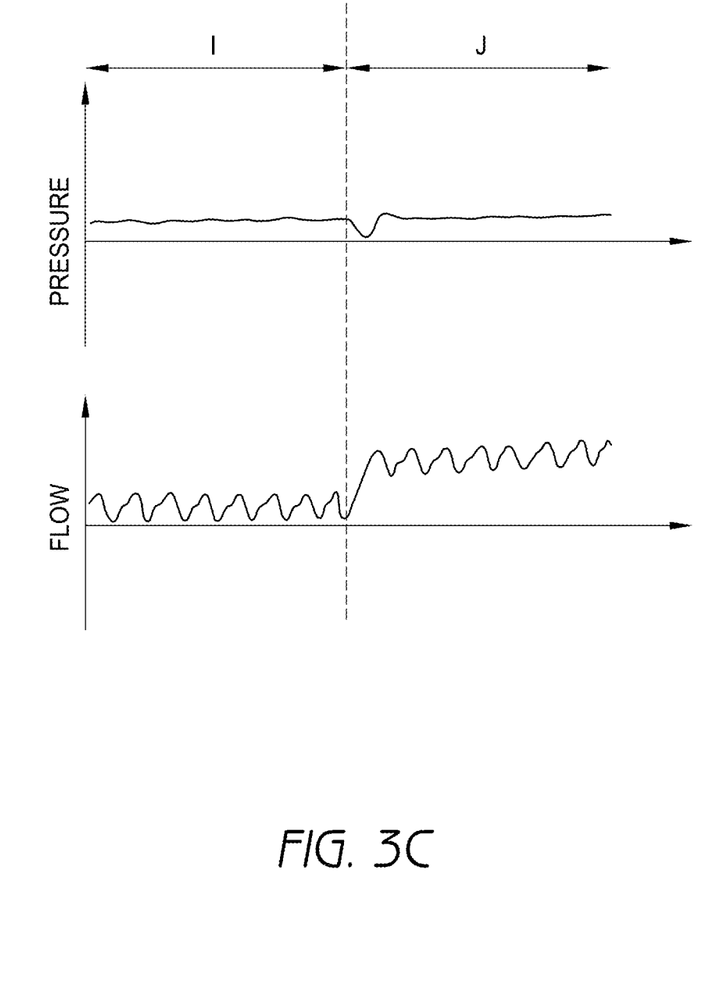
FIG. 3C is an example of a representative plot of pressure and flow against time for a part of a session of use of an apparatus using a pressure feedback control in a sub-therapeutic delivery mode and illustrates what happens when a leak develops.

FIGS. 3A and 3B illustrate the effect of a control operating according to preferred implementations of the present disclosure. For comparison, FIG. 3C illustrates the effect of a control operating according to a different principle under the same circumstances illustrated in FIG. 3A.

These plots are only intended to be representative and have been simplified accordingly.

In FIG. 3A, Part A shows normal breathing at the beginning of a session. The pressure is low (approximately 0 cmH2O) however the flow is averaging less than about 15 liters per min.

At Part B, the device responds to the low flow rate in Part A and increases the speed of the flow generator causing the flow and pressure to rise.

At Part C a leak is introduced (e.g., a mask leak occurs) and the level of flow increases. The pressure drops slightly due to this.

At Part D the algorithm responds to the increased level of flow by reducing the speed of the flow generator until the flow is again averaging approximately 15 liters per minute. The drop in speed further reduces the pressure.

In FIG. 3B, Part E shows normal breathing.

Part F illustrates a user having an apnoea. The apnoea can be clearly seen in the flattening of the flow signal.

At Part G, in response to the event in Part F, the device raises the pressure and normal breathing resumes.

The chaotic flow signal at the end of Part G indicates that the patient has woken and at Part H the pressure is reduced accordingly until the approximately 15 liters per minute average flow is maintained again.

FIG. 3C is a plot showing the effect of a device operating in pressure feedback mode under the same sequence of conditions as illustrated by FIG. 3A.

Part I shows normal breathing. The plots illustrate that there is minimal breath by breath fluctuation in pressure as the device is operating in pressure feedback mode.

A leak is introduced into the system at the end of Part I. Part J shows how the device responds to the drop in pressure by increasing the motor speed to maintain the pressure. The mean flow increases as a result of the increased motor speed. Eventually the increased flow acting against the resistance of the vent and leaking interface produces the desired pressure.

The behavior of the system in response to a leak can be compared to Parts B and C of FIG. 3A. In particular, in the control mode using average flow feedback, the flow was returned to the sufficient desirable level. Whereas, in the pressure feedback mode, the response to the developing leak resulted in an automatically increased flow.

The method as described may be adapted by further variations. A few of these variations have been described above and several more will be described here. This is not an exhaustive summary and many further variations and alternatives are possible without departing from the scope of the present disclosure.

According to one variation, the apparatus may monitor the measured flow, or pressure, or both, and other parameters which may indicate user respiratory rate. This controller may determine increased respiratory rate, or increased breath volume. In the presence of increased respiratory rate or breath volume, or both, the controller may increase the desired flow level in the sub-therapeutic mode. Increased respiratory rate or increased breath volume may be indicative of CO2 re-breathing. Increasing the desired flow level in the sub-therapeutic mode may adapt the sub-therapeutic mode flow level to account for prevailing system conditions.

The controller may further filter this response according to the present user sleep state to reduce or eliminate false positives due to dreaming, mask leaks and the like.

According to a further variation, the control program of the controller may include steps to check for occurrences of negative pressure in the user interface during the sub-therapeutic supply mode. For example, the control program of the controller may measure or calculate a mask or interface pressure on a continuous basis, or at least at a point in time or points in time during patient inhalation. If the mask or interface pressure drops below a predetermined threshold (preferably about 0 cmH2O or slightly below about 0 cmH2O) during patient inhalation, then the control program adapts the delivered therapy in an effort to reduce or eliminate these subzero pressures.

The control program may apply the adaption instantaneously (e.g., applied within a breath cycle) or over a longer time period (e.g., adjusting an inhalation boost parameter periodically).

The controller may derive of the mask pressure by providing a sensor at the mask to receive direct measurements of the internal pressure at the patient interface. Alternatively, the controller may predict a mask pressure from a measurement of the pressure of the delivered flow leaving the flow generator and a predicted pressure drop across the length of the supply conduit. The control program can predict the pressure drop over the length of the conduit on the basis of the instantaneous flow along the conduit. The control program can assume the conduit is a certain flow resistance, or can calculate the resistance of the conduit by implementing a pre-therapy test comparing delivered pressure and flow with no user interface connected to the conduit. The control program of the controller may implement any suitable method.

The control program may adapt the sub-therapeutic supply in a number of ways. One option would be to boost the target average flow. However, this may boost the peak pressures during patient exhalation, and will boost the overall average pressure, thereby reducing some of the comfort advantages intended by the present disclosure.

Alternatively, the controller can boost the supplied flow on patient inhalation, for example, by increasing the output of the flow generator at the start of inhalation and subsequently reducing the output of the flow generator back to a lower level for exhalation. The control program may monitor patient respiration to determine the start and end of inhalation by monitoring the variation in delivered flow or pressure on a breath-by-breath basis. While the average flow over multiple breaths is maintained substantially constant, the flow varies in an essentially sinusoidal manner in time with the patient breathing. The flow is higher during inhalation than during exhalation. The control program can determine the inhalation phase from this variation.

According to another variation, the control program of the controller may provide a settable parameter providing for a boosted inhalation flow. For example, a settable parameter may be provided on a scale. A value of 0 indicates no boost to the input parameter far the flow generator during inhalation relative to exhalation. A progressively higher value indicates a progressively higher boost to the input parameter of the flow generator used during inhalation relative to exhalation. The user or the user's physician could set the parameter according to measurement, or qualitative assessment of total breathing volume of the user, or according to reported instances of breathlessness during the sub-therapeutic supply phase.

The controller, while implementing the sub-therapeutic phase, may control a baseline input parameter to the flow generator according to the average delivered flow, and during periods of inhalation or periods of exhalation control the input parameter to the flow generator according to a combination of the baseline parameter and the settable inhalation boost. According to this, the baseline could be applied during inhalation or exhalation. If the baseline is applied during exhalation, then the inhalation parameter is a boost above the baseline. Where the baseline is applied during inhalation, the exhalation pressure is a reduction below the baseline according to the set parameter.

By boosting the flow (i.e., beyond the normal fluctuation provided by the patient breathing alone) during inhalation relative to exhalation, these variations avoid any feeling of starvation at the user interface.

According to a further variation, the control method may include control of humidification of the breaching gases (e.g., by varying a power input from a humidification heater 220) so humidification delivery in the sub-therapeutic mode is controlled independently of humidification delivery in therapeutic modes. For example but without limitation, the controller may reduce or disable humidification by reducing or turning off power to the humidification heater in the sub-therapeutic mode. The controller also may control the power input to the heated tube according to the mode. For example, the heater may supply less power to the conduit when in the sub-therapeutic mode.

According to a further variation, the apparatus may include a user selectable, or automatically initiated, test sequence. When the control program executes the test sequence, the control program causes the flow generator to deliver a controlled therapeutic pressure for a period of time. It is intended that the user will not consciously experience high mask pressures. The test sequence will provide an opportunity for the user to ensure that the mask is fitted correctly.

The control program may provide for a test sequence selectable by a user at the user interface, or may provide for the test sequence to automatically commence at the beginning of the session, or both.

The test sequence may provide for a pressure delivery at a preset minimum therapeutic pressure, a preset maximum therapeutic pressure, a preset test pressure, or another pressure selected according to previous use of the device (e.g., a 95th percentile pressure established from previous sessions).

The preferred embodiment of the apparatus, as described with reference to FIG. 2, includes a flow sensor and a pressure sensor. Each sensor may be of any known type.

The flow sensor may be a differential pressure sensor operating in conjunction with a flow restriction. In that case, parts of the differential pressure sensor may double as the pressure sensor.

In some configurations, an assessed pressure may be derived independently by a discreet pressure sensor. Alternatively, in some devices the delivered pressure may be inferred from blower speed, or calculated from a sensed flow and blower speed. An assessment of the delivered pressure also may account for an estimated pressure drop between the PAP apparatus and the patient, for example, by accounting for a pressure drop along the conduit according to a measured flow.

Similarly, where a pressure sensor is present, a flow sensor may not be required to assess flow. For example, flow may be inferred from blower speed and the output of a pressure sensor.

The disclosure has been described with reference to breathing gases supply devices particularly for use in the treatment of obstructive sleep apnea. PAP devices are also used in the treatment of other conditions, such as COPD, and may be used for the supply of mixed gases other than air, for example, a mixture of air and oxygen, a mixture of nitrogen and oxygen or the like. The method and apparatus of the present disclosure may be equally applied to gas supply apparatus for use in these other treatments.

What is claimed:

1. A respiratory therapy device comprising:
   a flow generator generating a flow of gas for delivery to a patient,
   at least one sensor for measuring properties of the flow of gas,
   a controller operatively connected to the flow generator and connected to the at least one sensor, the controller configured to cause the device to operate in:
      a flow control mode wherein the flow generator outputs the flow of gas at a substantially steady flow rate, or
      a pressure control mode wherein the flow generator outputs the flow of gas at a substantially steady pressure,
      wherein, when in the flow control mode, the controller is configured to analyze input from the at least one sensor and determine a flow rate value, and further configured to control the flow generator based on the determined flow rate value and a desired flow rate, and
      wherein, when in the flow control mode, the controller is configured to analyze input from the at least one sensor and derive an assessed pressure value, and wherein, in response to the assessed pressure value being above a pressure threshold, the controller is further configured to cause the device to switch from the flow control mode to the pressure control mode.

2. The respiratory therapy device of claim 1, wherein the desired flow rate is a single flow rate value.

3. The respiratory therapy device of claim 1, wherein the desired flow rate is within a flow rate range.

4. The respiratory therapy device of claim 3, wherein the controller is configured to check the determined flow rate value against an upper threshold and a lower threshold of the flow rate range.

5. The respiratory therapy device of claim 1, wherein the desired flow rate is determined based on an average flow rate across a predetermined number of preceding breaths or a predetermined time period.

6. The respiratory therapy device of claim 1, wherein the desired flow rate is a fixed predetermined value.

7. The respiratory therapy device of claim 1, wherein the desired flow rate is determined based on a type of patient interface used with the device.

8. The respiratory therapy device of claim 7, wherein the controller is configured to receive an input of the type of patient interface used with the device from a user.

9. The respiratory therapy device of claim 7, wherein the desired flow rate is determined based on a table of flow rate values for different types of patient interfaces.

10. The respiratory therapy device of claim 1, wherein, in response to the determined flow rate value being below the desired flow rate, the controller is configured to increase an output of the flow generator.

11. The respiratory therapy device of claim 10, wherein the controller is further configured to increase the output of the flow generator based on at least one of:
   a fixed predetermined incremental increase,
   an incremental increase that varies according to a current output of the flow generator, or
   an incremental increase that varies according to a difference between the determined flow rate value and the desired flow rate.

12. The respiratory therapy device of claim 1, wherein, in response to the determined flow rate value being above the desired flow rate, the controller is configured to decrease an output of the flow generator.

13. The respiratory therapy device of claim 12, wherein the controller is further configured to decrease the output of the flow generator based on at least one of:
   a fixed predetermined incremental decrease,
   an incremental decrease that varies according to a current output of the flow generator, or
   an incremental decrease that varies according to a difference between the determined flow rate value and the desired flow rate.

14. The respiratory therapy device of claim 1, wherein the at least one sensor comprises a flow sensor.

15. The respiratory therapy device of claim 1, wherein the at least one sensor comprises a pressure sensor.

16. The respiratory therapy device of claim 1, wherein the flow generator comprises a motor, wherein adjusting an output of the flow generator comprises adjusting a motor speed of the motor.

17. The respiratory therapy device of claim 1, further comprising a humidifier for humidifying the flow of gas before being delivered to the patient.

18. The respiratory therapy device of claim 17, wherein the humidifier is integrated within a housing of the flow generator.

19. The respiratory therapy device of claim 1, wherein, in response to the controller determining that the assessed pressure value is above the pressure threshold and causing the device to switch from the flow control mode to the pressure control mode, the controller is further configured to cause at least one of:

an alert to be shown on a user control interface of the device; and/or     recording, in a session data log maintained by the device, of the assessed pressure value having exceeded the pressure threshold.

20. The respiratory therapy device of claim 1, wherein, when in the pressure control mode, the substantially steady pressure is a therapeutic pressure.

* * * * *